US011045670B2

(12) United States Patent
Tito et al.

(10) Patent No.: US 11,045,670 B2
(45) Date of Patent: Jun. 29, 2021

(54) COSMETIC USE OF EXTRACTS DERIVED FROM SOMATIC EMBRYO ENRICHED PLANT CELL CULTURES AND COSMETIC COMPOSITIONS CONTAINING THOSE EXTRACTS

(71) Applicant: VITALAB S.R.L., Milan (IT)

(72) Inventors: Annalisa Tito, Naples (IT); Ani Barbulova, Naples (IT); Marida Bimonte, Naples (IT); Fabio Apone, Naples (IT); Gabriella Colucci, Naples (IT)

(73) Assignee: VITALAB S.R.L., Milan (IT)

( * ) Notice: Subject to any disclaimer, the term of this patent is extended or adjusted under 35 U.S.C. 154(b) by 520 days.

(21) Appl. No.: 15/569,537

(22) PCT Filed: Apr. 18, 2016

(86) PCT No.: PCT/EP2016/058486
§ 371 (c)(1),
(2) Date: Oct. 26, 2017

(87) PCT Pub. No.: WO2016/173867
PCT Pub. Date: Nov. 3, 2016

(65) Prior Publication Data
US 2018/0303749 A1     Oct. 25, 2018

(30) Foreign Application Priority Data

Apr. 29, 2015 (IT) .......................... MI2015A000614

(51) Int. Cl.
| | | |
|---|---|---|
| *A61K 36/752* | (2006.01) | |
| *A61K 36/896* | (2006.01) | |
| *A61K 36/73* | (2006.01) | |
| *A61Q 19/08* | (2006.01) | |
| *A01H 4/00* | (2006.01) | |
| *A61K 8/9789* | (2017.01) | |
| *C12N 5/04* | (2006.01) | |
| *A61K 36/738* | (2006.01) | |
| *A61K 36/48* | (2006.01) | |
| *A01H 6/78* | (2018.01) | |
| *A01H 6/54* | (2018.01) | |
| *A01H 6/74* | (2018.01) | |

(52) U.S. Cl.
CPC ............... *A61Q 19/08* (2013.01); *A01H 4/00* (2013.01); *A61K 8/9789* (2017.08); *C12N 5/04* (2013.01); *A01H 6/54* (2018.05); *A01H 6/749* (2018.05); *A01H 6/785* (2018.05); *A61K 36/48* (2013.01); *A61K 36/738* (2013.01); *A61K 36/752* (2013.01); *A61K 2800/805* (2013.01)

(58) Field of Classification Search
CPC .... A61K 36/752; A61K 36/73; A61K 36/896; A61K 2800/805; A61K 36/48; A61K 36/738; A61K 8/9789; A01H 4/00; A01H 6/54; A01H 6/749; A01H 6/785; A61Q 19/08; C12N 5/04
USPC ......................................... 424/736, 765, 773
See application file for complete search history.

(56) References Cited

U.S. PATENT DOCUMENTS

| 8,396,493 B2 * | 3/2013 | Boerries | ................. H04W 4/12 455/41.2 |
|---|---|---|---|
| 2011/0159121 A1 | 6/2011 | McDaniel | |

FOREIGN PATENT DOCUMENTS

| CN | 104812368 A | * | 7/2015 | ............... A01H 5/02 |
|---|---|---|---|---|
| WO | 2013102882 A2 | | 7/2013 | |

OTHER PUBLICATIONS

Barbulova et al. "Plant Cell Cultures as Source of Cosmetic Active Ingredients", Cosmetics, ISSN 2079-9284, www.mdpi.com/journal/cosmetics (Year: 2014).*
Mintel "Enriched Emulsion I" www.gnpd.com (Year: 2014).*
Day Cream 3000 Database GNPD Mintel, Oct. 2009.
Enriched Emulsion I, Database Mintel, Jan. 2014.
International Search Report of PCT/EP2016/058486 dated Jul. 18, 2016.

* cited by examiner

*Primary Examiner* — Aaron J Kosar
(74) *Attorney, Agent, or Firm* — Silvia Salvadori, P.C.; Silvia Salvadori (57) ABSTRACT

The present invention refers to a method for obtaining plant cell cultures, enriched of somatic embryos, a method of preparation of the extracts derived from these cell cultures, and the use of the obtained extracts in cosmetic compositions, targeted to treat imperfections related to skin aging and for inducing a skin tissue rejuvenation effect.

5 Claims, 7 Drawing Sheets

Fig. 1

A somatic embryo
enriched cell culture of
*Lotus japonicus*

A cell suspension culture of
*Lotus japonicus*

COSMETIC USE OF EXTRACTS DERIVED FROM SOMATIC EMBRYO ENRICHED PLANT CELL CULTURES AND COSMETIC COMPOSITIONS CONTAINING THOSE EXTRACTS

This application is a U.S. national stage of PCT/EP206/058486 filed on 18 Apr. 2016, which claims priority to and the benefit of Italian Patent Application No. MI2015A000614 filed on 29 Apr. 2015, the contents of which are all incorporated herein by reference in their entireties.

APPLICATION FIELD

The present invention refers to the cosmetic use of extracts derived from plant cell cultures induced to form somatic embryos, the method of preparation of those extracts and the relative cosmetic compositions containing those extracts for uses in dermo-cosmetics.

TECHNICAL BACKGROUND

Aging or skin senescence is an inevitable biological phenomenon, the timing and manner in which this occurs are predominantly affected by personal genetic background, but also by environmental factors and lifestyle.

The skin, the largest organ of the human body, is composed of three main layers that fulfill specific functions. The epidermis is the top layer of the skin and is mainly composed of keratinocytes, specialized cells that differentiate into corneocytes by accumulating keratin in their cytoplasm. Besides keratinocytes, melanocytes are also present in the epidermis, which cells are responsible for skin pigmentation, and cells of Langerhans, which are part of the immune system. The second layer, the dermis, is a connective tissue rich in blood vessels, immune cells and sensory receptors; it contains a matrix mainly composed of collagen fibers, elastin and hyaluronic acid, all important components which provide strength, hydration, flexibility and elasticity to the skin. Dispersed in the matrix, there are the fibroblasts, cells responsible for the synthesis of all the components that compose the dermis. The third layer is the hypodermis, located under the dermis, it is an adipose tissue, important as energy reserve for the entire organism.

The most dramatic changes that occur during skin senescence regard the dermis. With age, gradual thinning of the dermis thickness is observed: as consequence the skin loses its tone and elasticity, becomes weaker and wrinkles appear. This is due to the reduction of the number and the activity of fibroblasts, which lose their capacity to produce the components of the extracellular dermal matrix, in particular the collagen, that constitutes 75% of the human skin and is the main responsible for the physical properties of the dermis, such as strength and tone. 28 types of collagen have been identified, among which the most important are: type I collagen, which is the main structural component of the extracellular matrix of the dermis; type II collagen, present in high amounts in the cartilage, and type III collagen, present in the skin dermis and also localized in the blood vessel walls. The elastin fibers represent 5-10% of the total dermal fibers and are essential to ensure the skin elastic properties. Microfibrils of fibrillin are important for the functionality of the elastin fibers, as such components play a key role in the aggregation of the elastic fibers themselves; they are synthesized before the elastin and form a skeleton on which the elastin molecules are deposited. Subsequently, the microfibrils are moved to the periphery of the fiber in growth and form a sheath around the elastic fibers.

The reduction of the quantity and quality of the dermis matrix components, which is the main responsible for skin aging, is closely related to the ability of the fibroblasts to produce these components, and therefore to their state of health and senescence. During the last years, research has increasingly focused on the molecular components associated with the cellular longevity, including Sirtuins. The Sirtuins are proteins present in all multicellular organisms and regulate the activity of a wide variety of transcription factors and other proteins that bind DNA, thus acting as nucleus stability protection factors. Several pharmacological approaches have shown that the presence of high levels of these proteins in cells promotes longevity (Lavu et al., 2008). In fact, there are several studies showing that Sirtuin 1 protein (SIRT1), certainly the most studied and characterized among the Sirtuin family, is able to regulate the longevity of human cells and their internal metabolism (Zschoernig & Mahlknecht, 2008). In addition, the Sirtuin 6 (SIRT6) activates DNA repair, a role that is amplified in the presence of oxidative stress. Therefore, it acts as a central regulator of DNA repair, activating another enzyme factor, PARP1: increased SIRT6 expression in the cell leads to an increased activation of PARP1 in order to repair as quickly as possible the DNA damage (Mao et al., 2011). From these studies it has emerged that Sirtuins are key factors in the regulation of cell viability and in the slowing down of the cellular aging process, therefore appears more and more important to identify potential activators of these factors.

Recently, it has been identified a GDF11 protein (Growth Differentiation Factor 11), that is present in the blood of young organisms in larger quantities than in that of older organisms, in fact, its amount decreases with advancing of the age. The GDF11, encoded by a specific gdf-11 gene, is a member of the superfamily of "Transforming Growth Factor β" (TGFβ), and was initially identified for its regulatory role in embryonic development, in particular of the nervous system and anteroposterior regionalization (Williams, 2013; Anderson 2006). Recently, it was shown that GDF11 was able to reduce heart enlargement due to age (Loffredo et al, 2013), to revert the muscle aging (Sinha et al, 2014) and even reduce some deleterious effects due to the functional aging of the brain (Katsimpardiay et al., 2014). This sensational discovery has been validated by experiments in which the blood of a young mouse, containing the factor GDF11, was mixed with one belonging to an old rat, using a "parabiotic" system. The two mice were surgically joined in order to make possible the circulation of the blood of a young mouse into the body of an old mouse, or transfusions of blood of a young mouse in an aged mouse were carried out: in the old mouse was observed that the DNA of muscle cells was repaired and the muscle fibers became healthier and younger. Moreover, the muscle grip strength increased and the mouse was able to run longer on the tapis roulant compared to the untreated mice (Loffredo et al, 2013; Sinha et al, 2014).

Another group of researchers, using similar systems to transfer GDF11 from young mice to aged mice, observed that the animal cells in the subventricular zone, an area of the brain related to the sense of smell, received a higher flux of young blood, that not only improved the circulation in this region but also stimulated the production of new nerve cells. The sense of smell of the older mice was significantly improved, inverting the normal sensory loss associated with aging. The most interesting discovery about this work was that the increasing of the blood flow was observed not only in the brain regions related to smell, but also in the entire brain (Katsimpardiay et al., 2014).

Recently, the tendency of the cosmetic market has been orientated to products of natural plant origin and in fact, numerous and diversified examples already exist. Plants are unique organisms able to create their own food through photosynthesis, providing oxygen to the atmosphere at the same time. They are also important sources of food and therapeutic compounds for all other living organisms. The plants are remarkable for their great synthetic versatility: the spectrum of chemical structures synthesized by the plant kingdom is broader than that of any other group of organisms, making the plants the main source of natural remedies in the pharmaceutical, food and cosmetics (Fowler, 1984). Humans developed an extensive knowledge about useful plants during history, through a constant contact with the natural environment, and the use of plants and plant extracts in traditional medicine has been known since ancient times.

Plant cell cultures represent a viable alternative for the production of cosmetic and dermatological active ingredients, since they allow to obtain contaminant-free products, biosustainable and standardized, whose production can easily be extended on an industrial scale (Lee et al, 2010). There are numerous advantages of using plant cell cultures as a source of active ingredients respect to the use of plants grown in the field: 1) continuous supply of fresh material, regardless of the seasons or the reproductive cycle of the plant; 2) the growing conditions can be easily standardized in order to have higher level of consistency from batch to batch; 3) the extracted components are safe and clean, which means that there is no risk of pathogenic or environmental contamination; 4) the production system is highly sustainable: it is not necessary any agricultural land, there is less water consumption and less waste material; 5) it is a very versatile system since the cells can be induced to differentiate or produce more of a certain metabolite, simply by changing the growth conditions, or by adding different substances in the culture medium (Barbulova et al, 2014).

Despite the plant cell cultures represent a valuable source of extracts with proven cosmetic efficacy, they may have some limitations due to their totipotency and undifferentiated state, and not to be the most suitable system for the production of some classes of actives with more specific applications. Instead, the differentiated plant tissue cultures (eg, root cultures, somatic embryos, shoots, etc.) are highly specialized and differentiated, and therefore are able to synthesize compounds which are not produced in any other plant organ.

Somatic embryogenesis is a process by which the somatic cells, either differentiated or undifferentiated, are induced in the laboratory to generate embryogenic cells that, through a series of morphological and biochemical changes (Quiróz-Figueroa et al., 2006), form bipolar structures without vascular connection with the original tissue. These structures are called somatic embryos, because they are morphologically and physiologically identical to zygotic embryos, namely those present in the seeds of the plant.

All developmental processes of the somatic embryos are regulated by different factors, including plant hormones, enzymes and other secondary metabolites related to the somatic embryogenesis. Being young structures in constant mitotic activity, the somatic embryos could be an excellent source of cosmetic active ingredients with the effect of rejuvenation and slowing down the aging process in human skin.

INVENTION SUMMARY

The authors of the present invention have developed a method of production and extraction of somatic embryos in liquid culture, and in that way have identified three types of extracts, that both individually and synergistically by molecular mechanisms, are able to slow down and revert the phenomenon of aging of skin cells by acting specifically on GDF11 and Sirtuins. Therefore, the cosmetic compositions based on these extracts should have a general effect of rejuvenation in the skin senescence.

In an aspect thereof, the present invention refers to the cosmetic use of at least one extract derived from plant cell cultures enriched in somatic embryos for the treatment of skin aging related imperfections and for producing a rejuvenation effect in the skin.

The above plant cell cultures enriched in somatic embryos are preferably plant cell cultures belonging to the species *Lotus japonicus, Citrus limon* and *Rosa gardenia*.

In another aspect, the present invention relates to a process for the preparation of at least one extract from plant cell cultures enriched in somatic embryos, preferably belonging to the species *Lotus japonicus, Citrus limon* and *Rosa gardenia*, comprising the following steps:

a) inducing plant cell suspension cultures to form somatic embryos;

b) homogenizing the obtained somatic embryos in aqueous saline solution, obtaining a homogenate;

c) separating the solid part from the liquid part of the obtained homogenate, the liquid part constituting a hydrosoluble extract.

The above plant cell cultures are obtained by taking tissues from plants, induction of callus formation on a solid substrate, suspension of the obtained callus in liquid culture.

The above mentioned aqueous saline solution is generally a buffered solution, such as phosphate saline buffer PBS at pH 7.4.

Preferably, the above mentioned step c) of separating the solid part of the homogenate from the liquid part is performed by centrifugation and leads to the separation of a supernatant (liquid part) and a pellet (solid part).

The process, according to the invention, may also comprise the further step of extracting the solid part by using a lipophilic solvent, obtaining a liposoluble extract. The lipophilic solvent is an organic solvent preferably selected from alcohols, acetone, ether, sterols and oils and conveniently constituted by an alcohol of 2-4 carbon atoms, preferably ethanol.

Alternatively, the process according to the invention may comprise the further step of treating the solid part with proteolytic enzymes in acid solution, in order to hydrolyze the proteins from the cell walls of the somatic embryos, obtaining an extract rich in peptides and sugars.

Preferably the solid part is previously treated with distilled water to remove the residues of cytoplasmic components and then treated with an acid solution for the hydrolysis of the glucosidic bonds, and with enzymes to hydrolyze the proteins from the cell walls.

Preferably, after the treatment with distilled water and before the treatment with the acid solution, the solid part is treated with EDTA solution (for example 2 mM) and boiled.

The above-mentioned extracts (hydrosoluble extract, liposoluble extract and the peptides/sugars rich extract) can be evaporated to dryness with known methods (for example using a lyophilizer, a rotary evaporator or a spray-drier), obtaining, depending on the case, a powder or a semi-solid paste.

Further aspect of the present invention refers to the cosmetic use of the extracts as defined above, where the above-mentioned at least one extract is selected from the hydrosoluble extract, the liposoluble extract or the extract rich in peptides and sugars, obtained by the above described process.

Preferably, for the cosmetic use the combination comprises at least one of the above mentioned extract, or two of them or preferably all three.

Further aspect of the present invention refers to a composition comprising all three of the above extracts: hydrosoluble extract, liposoluble extract and the extract rich in peptides and sugars.

Preferably the mentioned composition contains, for one part by weight of the hydrosoluble extract, from 0.01 to 100, preferably 1, parts by weight of the liposoluble extract and independently, from 0.01 to 100, preferably 0.1, parts by weight of the extract rich in peptides and sugars.

Preferably, the composition according to the invention further comprises at least one hydrophilic solvent selected from the group comprising water, aqueous salt solutions and organic solvents, preferably oils, alcohols, glycerol, organic acids, amides, amines, aldehydes and ketones.

Furthermore, the present invention refers to the use of the cosmetic composition described above for the treatment of imperfections linked to skin aging and for producing a skin rejuvenation effect.

Finally, the present invention refers to a cosmetic formulation comprising one of the extracts described above (hydrosoluble extract, liposoluble extract, extract rich in peptides and sugars) or a composition as defined above and a cosmetically acceptable vehicle. Such cosmetic formulation may be for example in the form of cream, gel, lotion for skin application, lipstick, foundation cream and make-up.

DETAILED DESCRIPTION

According to one embodiment of the present invention, the process is performed according to the following procedures and conditions:

Callus preparation: whole leaves are taken from plants, for example, *Lotus japonicus*, and sterilized with 70% ethanol (in water v/v) for 15 minutes, and sodium hypochlorite 1% (in water v/v), for additional 15 minutes. After being washed 3 times in water to remove the alcohol and hypochlorite, leaves are cut into pieces of about 0.5 cm² each with a sterile blade. All of leaf fragments are placed on a solid medium Gamborg B5 medium containing: plant agar 7.5 mg/L, myo-inositol 500 mg/L, sucrose 30 g/L, 2.4D 1 mg/L, kinetin 0.01 mg/L, adenine 1 mg/L, pH 5.7. After about 5 weeks of incubation at 20° C. in the dark, calluses are obtained due to the proliferation of the cells of the leaf. The calluses are then transferred to fresh culture medium every 3-4 weeks.

a) Cell culture preparation: when the calluses reach a diameter of about 1 cm (about 50 mg of weight), they are picked up and dispersed in Erlenmeyer flasks containing 50 ml of liquid culture medium AB1 (Gamborg B5 medium containing: myo-inositol 500 mg/L, sucrose 30 g/L, 2.4D 1 mg/L, kinetin 0.01 mg/L, adenine 1 mg/L, pH 5.7). The flasks are placed in the dark on an orbital shaker with 100 rpm shaking speed. After about 10 days, calluses break up and proliferate to form cell suspension cultures.

b) Somatic embryo preparation: the plant cell cultures are resuspended in a fresh liquid growth medium AB2 (Gamborg B5 medium containing: myo-inositol 500 mg/L, sucrose 30 g/L) with addition of phyto-hormones Thidiazuron (TDZ) 1 mg/L, and benzylaminopurine (BAP), 0.05 mg/L, glutathione 10 mg/L, casein 500 mg/L, ammonium phosphate and ammonium sulfate, 7% and 10%, respectively, to induce the formation of somatic embryos in the cell cultures.

c) Somatic embryo cell cultures growth: the induction of somatic embryos is conducted for 4 weeks, adding fresh culture medium every week, until reaching a level of differentiation into somatic embryos of about 70-90%.

d) Somatic embryo treatments: according to a preferred embodiment of the method disclosed in the present invention, the somatic embryos may be subjected to physical treatments (heat, cold, UV) during their growth or treated with chemical compounds (proteins, lipids, sugars, salts, small organic molecules, physical factors) to induce the expression of larger amounts of secondary metabolites with antioxidant properties.

e) Somatic embryo collection: the separation of the embryos from the growth medium can be carried out by centrifugation at 2000 g, sedimentation or filtration through membranes with a pore diameter smaller than 100 microns. The embryos are then frozen at −80° C. to preserve their chemical and physical properties.

f) Somatic embryo homogenization: frozen somatic embryos are broken mechanically (homogenized) in the presence of saline phosphate PBS buffer (136 mM NaCl, 2.7 mM KCl, 12 mM $NaH_2PO_4$, $KH_2PO_4$ 1.76 mM, pH 7.4) in the ratio of 1:2 w/v. This step can be carried out in a suitable container such as a ceramic mortar and ceramic pestle, previously cooled, or for larger volumes, larger containers may be used, even metal, where the plant material can be homogenized with metal blades, using both laboratory or industrial blenders, or presses.

g) Obtainment of the hydrosoluble extract: once obtained a homogeneous lysate by homogenization of the embryos, the sample is centrifuged, for example at 4000 rpm for about 15 minutes at 4° C., to precipitate the insoluble components. The supernatant obtained by centrifugation is collected: it constitutes the hydrosoluble extract.

h) Obtainment of the liposoluble extract: half of the pellet obtained by centrifugation is treated with an organic solvent (alcohol, acetone, ether, oil) and mixed in order to extract the oil soluble components (together with those poorly soluble in water), at temperatures comprised between 20 to 80° C. depending on the kind of solvent used. After further centrifugation at 4000 rpm for 15 min at 4° C., the liquid phase is removed: it constitutes the liposoluble extract.

i) Obtainment of the extract rich in peptides and sugars from the cell walls: the other half of the pellet (containing cell walls) obtained in step h) is further washed with distilled water to remove the residue of the soluble fraction and filtered again. The pellet is weighed, suspended and boiled with 2 volumes (ratio w/v) of a 2 mM EDTA solution for 20 minutes. After cooling, the extract is filtered through filter cloth, washed and filtered again to remove residual EDTA. Subsequently, the obtained pellet is boiled under a chemical hood with 2 volumes of a 0.1N HCl solution for 1 hour in order to hydrolyze the sugar bonds. After boiling, the sample is suspended again, cooled in ice and then enzymatically digested at 37° C. for 16 hours with pepsin, using 1 mg of enzyme per each ml of suspension. At the end of the enzymatic digestion, the suspension is centrifuged or filtered again to obtain a transparent solution: it constitutes the extract rich in peptides and sugars derived from the cell walls.

The extracts obtained in steps h), i) and j) are dried in a lyophilizer, roto-evaporator, drying chamber or spray-dryer to remove the solvent. The powder or the resulting semi-solid paste is suspended in water (hydrosoluble fraction and peptide/sugar fraction) or in organic solvents compatible with cosmetic formulations (liposoluble fraction) to the desired concentration. In the case in which the solvent used in step i) is an oil, such as a triglyceride, it cannot be removed, therefore the obtained solution already constitutes the active ingredient for use in formulas for cosmetic and dermatological applications.

The obtained solutions containing the different fractions (hydrosoluble, liposoluble and that of peptides/sugars) may be further dissolved in an appropriate volume of glycerol or another solvent (oil, alcohol, sterol), depending on the chemical characteristics of the fraction, in order to have a concentration ranging from 0.1% to 10% (w/v). These solutions represent the raw material that is added to the manufacture formulations of cosmetic or dermatological products ready for applications.

In conclusion, the subject-matter of the present invention consists of: the hydrosoluble extract of somatic embryos obtainable by the method steps from a) to h); the liposoluble extract obtainable by the method steps from a) to i); and the extract of peptides and sugars from the cell walls obtainable by the method steps from a) to j). Furthermore, the invention also refers to the preparation method of the above somatic embryos by induction with specific growth conditions and treatments developed by the Applicant, which allow to obtain the described extracts rich of substances with beneficial action on skin cells.

The object of the present invention are also cosmetic compositions comprising the hydrosoluble extract, the liposoluble extract and extract rich in peptides and sugars from the cell walls, alone or in combination.

Advantageously, such cosmetic compositions contain, for each part by weight of hydrosoluble extract, 0.01 to 100 parts, preferably 1, parts by weight of liposoluble extract and 0.01 to 100 parts by weight, preferably 0.1, of extract rich in peptides and sugars, possibly along with vehicles, excipients and/or cosmetically acceptable adjuvants.

A particularly preferred cosmetic composition comprises, for one part by weight of hydrosoluble extract, one part by weight of liposoluble extract and 0.1 parts by weight of extract rich in peptides and sugars, possibly together with cosmetically acceptable vehicles, excipients and/or adjuvants.

Such compositions may be in the form of creams, gels, cosmetic lotions for the skin application, as well as lipsticks, foundation creams and make-up. Vehicles that can be used are liposomes, preferably multilamellar liposomes, cyclodextrins, silicates. Finally, the invention refers to a cosmetic treatment method for the rejuvenation and the slowing down of the cutaneous senescence process comprising the application on the skin of a cosmetically effective amount of a composition as described above, i.e. comprising at least one of these extracts derived from somatic embryo cultures.

The present invention will be now described for illustrative and non-limiting purposes, according to preferred embodiments thereof, with particular reference to the figures of the accompanying drawings, in which.

In order to describe the present invention for illustrative and non-limiting purposes, some examples relative to the preparation of somatic embryo cell cultures of the species *Lotus japonicus, Citrus lemon* and *Rosa gardenia* (var. *Maipaleo*) are herein provided. Moreover, an example of preparation of an hydrosoluble extract, a liposoluble extract and an extract rich in peptides and sugars from *Lotus japonicus* somatic embryos and experiments that demonstrate the biological activity of the above mentioned extracts in the cosmetic field are provided too.

EXAMPLE 1

Figure 1:
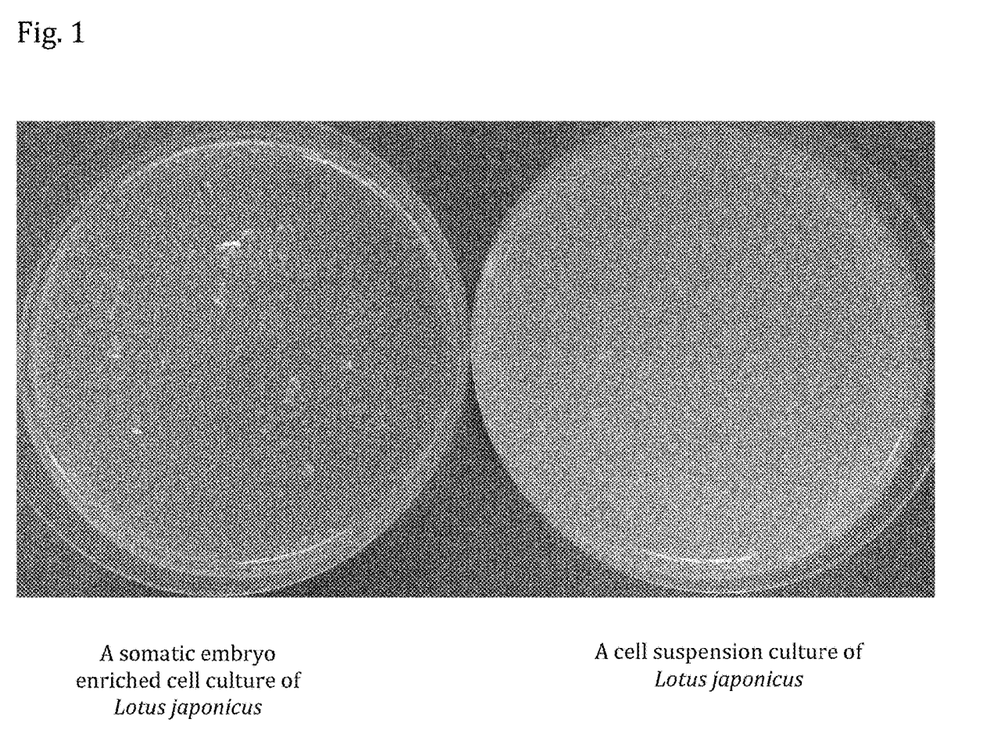
FIG. 1 shows a non-differentiated plant cell culture and an somatic embryo-enriched cell culture of *Lotus japonicus*, both after 4 weeks of growth.

Preparation and Growth of *Lotus japonicus, Citrus lemon* and *Rosa gardenia* (Var. *Maipaleo*) Somatic Embryo Cell Cultures Pieces of young leaves of *Lotus japonicus, Citrus lemon* and *Rosa gardenia* were used for callus formation on solid medium, and subsequently liquid cell cultures were induced to form somatic embryos. The observation of samples of non-induced cell cultures and cell cultures induced to form somatic embryos, made it evident that, after 4 weeks of growth, cells in the induced culture were differentiated and aggregated to form embryo-like structures, which made the culture more grainy compared to that of non-induced cells (FIG. 1). Once dense cultures of somatic embryos from the 3 different species were obtained, the percentage of differentiation after 4 weeks was evaluated by observation on optical microscope, and staining with methylene blue in 0.01% aqueous solution. For *Lotus japonicus* cell culture a yield of differentiation of 90% was calculated, 80% for *Citrus lemon* cell culture and 72% for *Rosa gardenia* cell culture. Once the desired density was reached, the somatic embryos were harvested and processed in order to obtain the extracts. The method used was as follows:

Obtaining Cell Cultures of Somatic Embryos and Harvesting.

50 mg of plant callus were suspended in Erlenmeyer flasks containing 50 ml of AB1 liquid culture medium (Gamborg B5 medium containing: myo-inositol 500 mg/L, sucrose 30 g/L, 2.4D 1 mg/L, kinetin 0.01 mg/L, adenine 1 mg/L, pH 5.7). The flasks were placed in the dark on a shaker with orbital shaking of 100 rpm to obtain a dense plant cell culture. After about 10 days, a dense culture of somatic embryos, obtained by the proliferation and differentiation of the callus cells were observed. 100 ml of dense culture was inoculated into 1 L of a half AB/TDZ medium to allow their growth. After 10 days, the plant cell cultures were suspended in a new AB2 liquid growth medium (Gamborg B5 medium containing: myo-inositol 500 mg/L, sucrose 30 g/L) with addition of the phyto-hormones Thidiazuron (TDZ), 1 mg/L, and benzyl-aminopurine (BAP), 0.05 mg/L, glutathione 10 mg/L, 500 mg/L casein, ammonium phosphate and ammonium sulfate, 7 and 10%, respectively, to induce the formation and development of the somatic embryos (cell cultures enriched with somatic embryos). After 4 weeks of growth, the somatic embryos were harvested by removing by filtration their culture medium and frozen at −80° C.

EXAMPLE 2

Preparation of Different Extracts from Somatic Embryo Cell Cultures of the Species *Lotus japonicus, Citrus lemon* and *Rosa gardenia*

The harvested somatic embryos were processed in order to obtain extracts with different chemical characteristics. 3 types of extracts from somatic embryo cell cultures belonging to the species *Lotus japonicus, Citrus lemon* and *Rosa gardenia* were obtained. For each of the species the following extracts were prepared: a) an extract of water-soluble compounds (hydrosoluble extract), obtained by the use of a water-based saline buffer (PBS); b) an extract of lipophilic compounds which is able to dissolve in non-polar or poorly polar solvents, obtained by using ethanol; c) an extract composed of peptides and sugars derived from the cell walls, obtained by the already described procedure. The obtained extracts were treated in order to eliminate the solvent (water or ethanol in the specific case) by lyophilization or vacuum evaporation. The obtained powders or semi-solid gels were weighed and dissolved in distilled water to the desired concentration in order to be assayed on skin cell cultures.

The method used for the extract preparation is described as follows:
Preparation of the Aqueous, Ethanol and Peptide/Sugar Extracts.

500 g of frozen somatic embryos were lysed mechanically and then homogenised in the presence of PBS (136 mM NaCl, 2.7 mM KCl, 12 mM $NaH_2PO_4$, 1.76 mM $KH_2PO_4$, pH 7.4) at a ratio of 1:2 volume/weight. The obtained homogenate was centrifuged at 8,500 rpm for 15 minutes at 4° C. to precipitate the insoluble components. The supernatant, obtained from the centrifugation, constitutes the hydrosoluble extract and was frozen at −20° C. Subsequently, the hydrosoluble extract was lyophilized for 3 days to obtain a powder that was suspended in water at a concentration ranging between 1 and 10% for further use in biological assays.

Half of the pellet was treated with an organic solvent (alcohol, acetone, ether or other non-polar solvents), compatible with the basic emulsions used for cosmetic formulas, under constant stirring in order to extract the liposoluble components. After centrifugation at 6000 rpm for 15 min at 4° C., the liquid phase, that constituted the liposoluble extract, was used in the biological assays.

The other half of the pellet was further washed with water and filtered again. The pellet was weighed, suspended and boiled in 2 volumes of a 2 mM EDTA solution for 20 minutes. After cooling the extract was filtered through filter cloth, washed and filtered again to remove residual EDTA. Subsequently, the obtained pellet was boiled in 2 volumes of 0.1 N HCl solution for 1 hour in order to hydrolyze the sugars. After boiling, the sample was ice cooled and then digested with pepsin at 37° C. for 16 hours, using 1 mg of enzyme per ml of suspension. The obtained extract of peptides and sugars was lyophilized for 3 days to obtain a powder that was dissolved in water at a concentration ranging from 1 and 19% for further testing.

EXAMPLE 3

Biological Assays of Somatic Embryo Cell Cultures Derived Extracts on Skin Cells As an illustrative and non-limiting example of the present invention, *Lotus japonicus* somatic embryo extracts have been used to elucidate the beneficial and therapeutic properties on skin cells. The hydrosoluble extract, the liposoluble one (ethanolic) and the one composed of peptides and sugars, deriving from the cell walls, were tested on HDF cells (Human Dermal Fibroblasts) in order to evaluate the cosmetic activity. The methods used in the assays and the obtained results are described hereinafter.
Methods Used:
Cytotoxicity Assay.

This assay is based on the use of MTT [3-(4,5-dimethylthiazol-2-yl)-2,5-diphenyltetrazolium bromide] for the first time described by Mosmann in 1983. It is based on the capacity of the enzyme mitochondrial dehydrogenase of the viable cells to hydrolyze the MTT tetrazolium ring (light yellow) and to form crystals of formazan (dark blue color). These crystals are impermeable to cell membranes and accumulate in the cytoplasm of metabolically active cells. The number of live and healthy cells is thus directly proportional to the level of formazan product. HDF cells, in the initial number of $1.5 \times 10^4$ per well, were grown in 96-well plates in DMEM culture medium (Lonza), supplemented with 10% Fetal Bovine Serum, for about 20 hours. After treatment with different concentrations of the mixture for 48 hours, the cells were washed in PBS and incubated with 100 μl/well of "reaction buffer" containing: 10 mM Hepes, 1.3 mM $CaCl_2$, 1 mM $MgSO_4$, 5 mM glucose and 0.5 mg/ml MTT colorimetric substrate in PBS buffer at pH 7.4. After 3 hours of incubation at 37° C., 5% $CO_2$, 100 μl of solubilizing solution containing 10% Triton-X100, 0.1N HCl in absolute isopropanol was added to each well. After 30 minutes, the colorimetric reaction was measured at 595 nm with an ELISA plate reader.
Expression Analysis of Genes GDF11, SIRT1, SIRT6, Col-III, ELN and FBn1.

HDF cells, in the initial number of $7 \times 10^4$ per well, were grown in 6-well plates in DMEM culture medium (Gibco), supplemented with 10% Fetal Bovine Serum (FBS) for 20 hours. The cells were then incubated with the extracts for 6 hours in serum free medium. For cell RNA extraction a kit purchased from Ambion/Life Technologies was used. After the treatments, cells were washed with PBS, dissolved in lysis buffer and subjected to the extraction procedure according to the kit protocol. The RNA samples were subjected to a treatment with DNase I (Ambion) to remove genomic DNA contaminants. 2 μL of each sample were loaded on 1% agarose gel in the presence of denaturating "loading dye" and quantized using specific RNA markers (Thermo Scientific) as a reference. For quantification, Gene software tools (Perkin Elmer) was used. 300 ng of total RNA was reverse transcribed using the enzyme reverse transcriptase (Thermo Scientific). The reactions of semi-quantitative RT-PCR were performed using internal standards as the universal primer pair 18S primer/competimer (Ambion) in ratio 4:6. The PCR products were separated on 1.5% agarose gel, visualized using the Geliance (Perkin Elmer) tool and analyzed by densitometry using the GeneTools software. The values shown in the graphs represent the ratio of the band intensity relative to the gene in analysis and that of the band relative to the 18S standards, thus getting a value related to the actual expression of the gene of interest, and not one dependent on the amount of RNA or PCR reagents present in that sample. The values were then converted into a percentage (%), by establishing the value obtained from the untreated control as 100%.

Obtained Results

Evaluation of the Most Suitable Extract Concentrations to Use in Cell-Based Assays.

Figure 2:
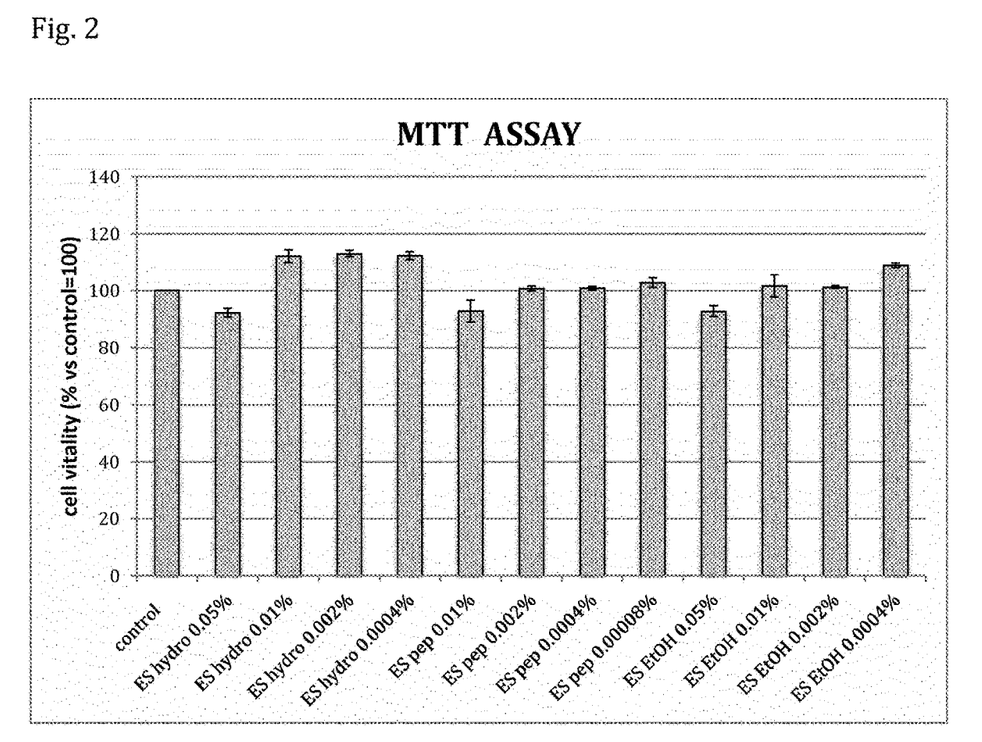
FIG. 2 shows the MTT assay showing that the *Lotus japonicus* somatic embryo extracts are not cyto-toxic at all the tested concentrations. In the ordinate they are reported the number of viable cells, expressed as percentage respect to the control, established as 100%.

In order to determine the concentrations of the various Lotus somatic embryo extracts to be used in the bioassays, increasing concentrations of the extracts were tested and the maximum non-cytotoxic dose for growing skin cell cultures was determined. For the aqueous and ethanolic extract, concentrations ranging from 0.05% to 0.0004% were tested, while for the mixture of peptides and sugars concentrations from 0.01% to 0.00008% were used. As shown in FIG. 2, none of the tested concentrations showed any significant cytotoxic effect on the cells.

Effects of the Aqueous, Ethanol and Sugars/Peptides Extracts Derived from of *Lotus japonicus* Somatic Embryos on the Gene Expression of GDF11, SIRT1 and SIRT6.

Figure 3:
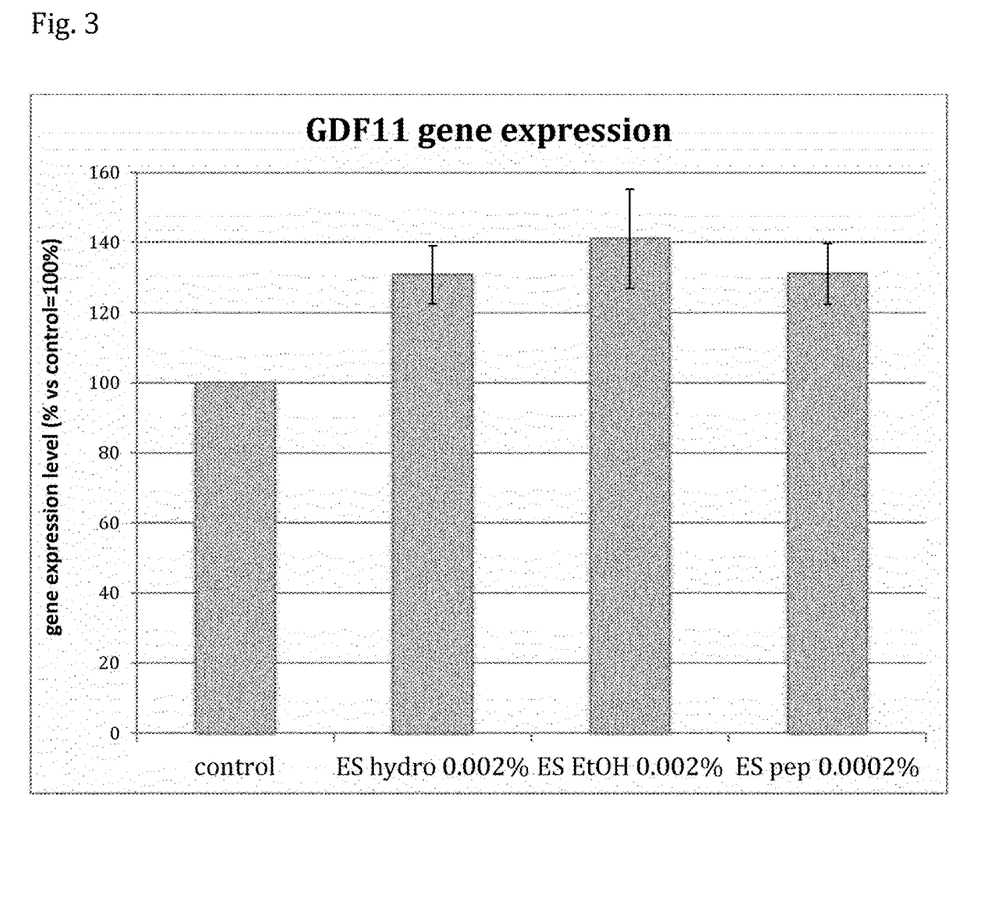
FIG. 3 shows the expression analysis of GDF11 gene in cells treated with the *Lotus japonicus* somatic embryo extracts compared with that of untreated control cells. The values shown in the graph are expressed as percentages compared to the untreated control sample (established as 100%).

Nevertheless there were not reported studies of GDF11 on skin cells, the authors of the present invention carried out some preliminary investigations and found that GDF11 was produced and regulated in skin cells, thus very likely it might have similar functions related to the anti-senescence activity. In order to determine whether the *Lotus* somatic embryo extracts had an effect on the expression of the GDF11 gene, HDF were treated with the water-soluble extract (0.002%), the ethanolic extract (0.002%) or the mixture of peptides and sugars (0.0002%) for 6 hours. After the treatments, the cells were harvested and processed for RNA extraction. The gene expression was assessed by RT-PCR. As shown in FIG. 3, all three analyzed extracts significantly stimulated the expression of the GDF11 gene by around 30%.

Figure 4:
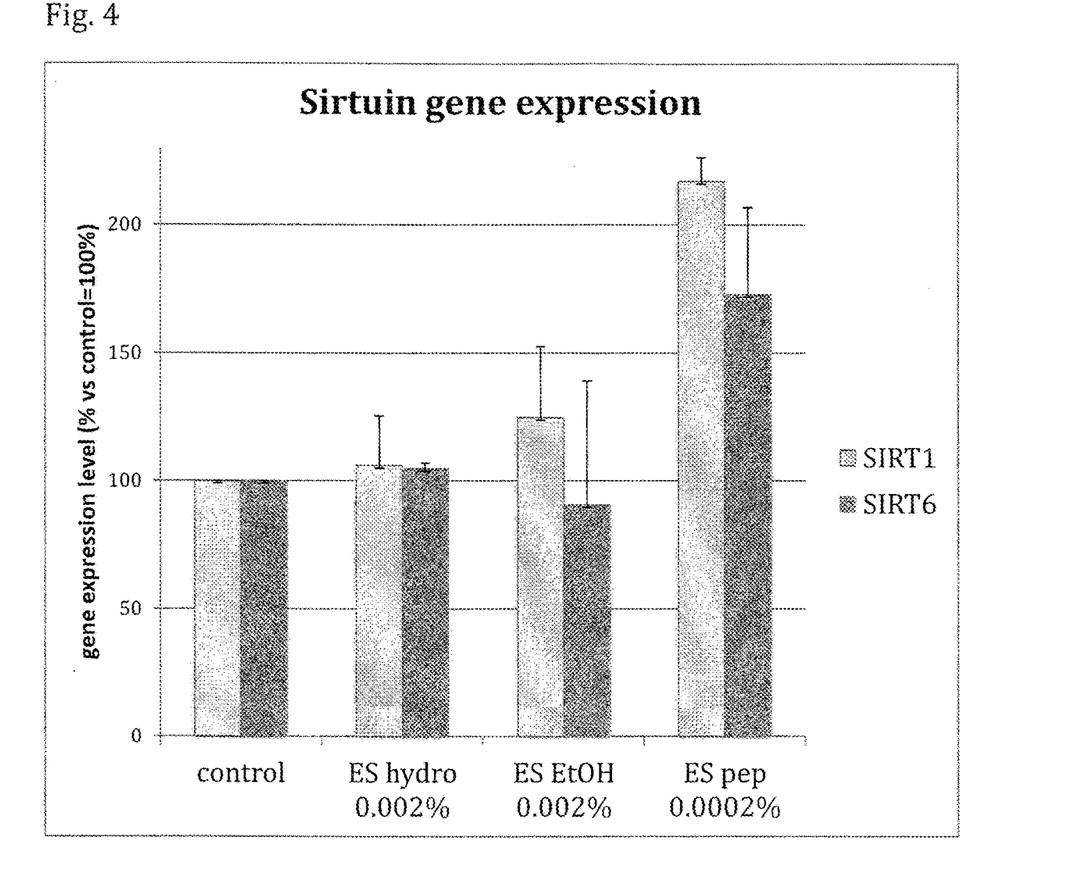
FIG. 4 shows the expression analysis of the genes Sirtuin 1 (SIRT1) and Sirtuin 6 (SIRT6) in cells treated with the *Lotus japonicus* somatic embryo extracts compared with that of untreated control cell samples. The values shown in the graph are expressed as percentages compared to the untreated control sample (established as 100%).

After verifying the effect of the extracts on the expression of GDF11, it was evaluated their effect on the expression of SIRT1 and SIRT6 genes, encoding the two Sirtuins having roles in promoting longevity and the cell health, by RT-PCR experiments on HDF treated with the extracts. As shown in FIG. 4, the peptide/sugar mixture produced a significant increase in the expression of both genes, +117% for sirt1 and 73% for sirt6. Instead, the effect of the ethanol extract on sirt1 was very modest. These results indicated that the extract of peptides and sugars derived from the cell walls of the *Lotus* somatic embryos was the most effective in promoting cellular rejuvenation by increasing GDF11 and Sirtuin expression.

Effects of the Aqueous, Ethanol and Sugar/Peptide Extracts Derived from *Lotus japonicus* Somatic Embryos on the Gene Expression of Col-III, ELN and FBn1.

In order to determine whether the *Lotus* somatic embryo extracts had an effect on the genes responsible for the production of the Extra Cellular Matrix (ECM) proteins, the expression of the genes of type III collagen, elastin and fibrillin was assessed by RT-PCR on HDF.

Figure 5:
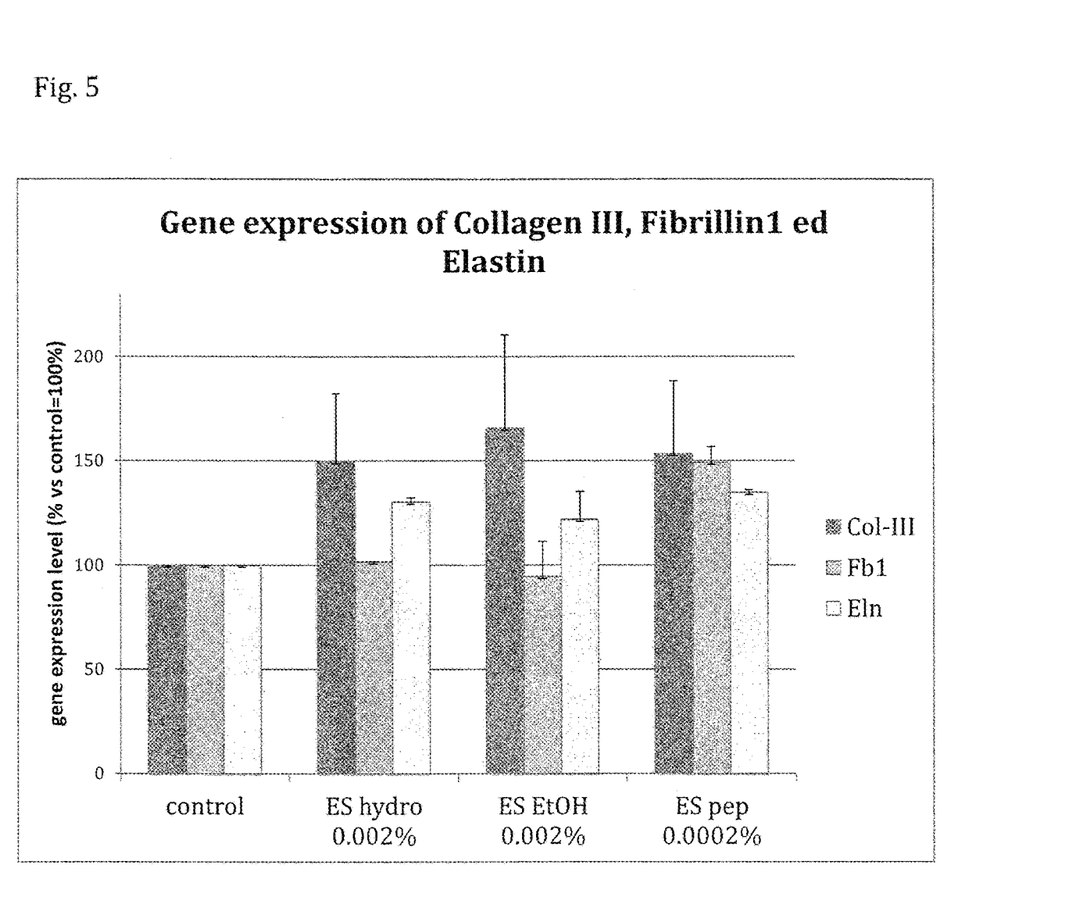
FIG. 5 shows the effect of *Lotus japonicus* somatic embryo extracts on the gene expression of collagen III (Col-III), Fibrillin 1 (Fb1) and Elastin (Eln), after 6 hours of treatment; the values shown in the graph are expressed as percentages relative to the untreated control sample, established as 100%.

As shown in FIG. 5, all three extracts produced a significant effect on the synthesis of collagen III by around 70%. The expression of the elastin gene was increased by about 30% in cells treated with the water-soluble extract or with the mixture of peptides/sugars, while on fibrillin 1 only the mixture of peptides and sugars determined an increase of 50%. These data demonstrated that the extracts derived from *Lotus* somatic embryos had a stimulating effect on the proteins of the extracellular matrix, in particular, the extract of peptides and sugars derived from the cell walls was effective on all the 3 analyzed genes.

Effects of the *Lotus japonicus* Somatic Embryo Sugar/Peptide Extract on the GDF11 Expression in Aged Fibroblasts.

Figure 6:
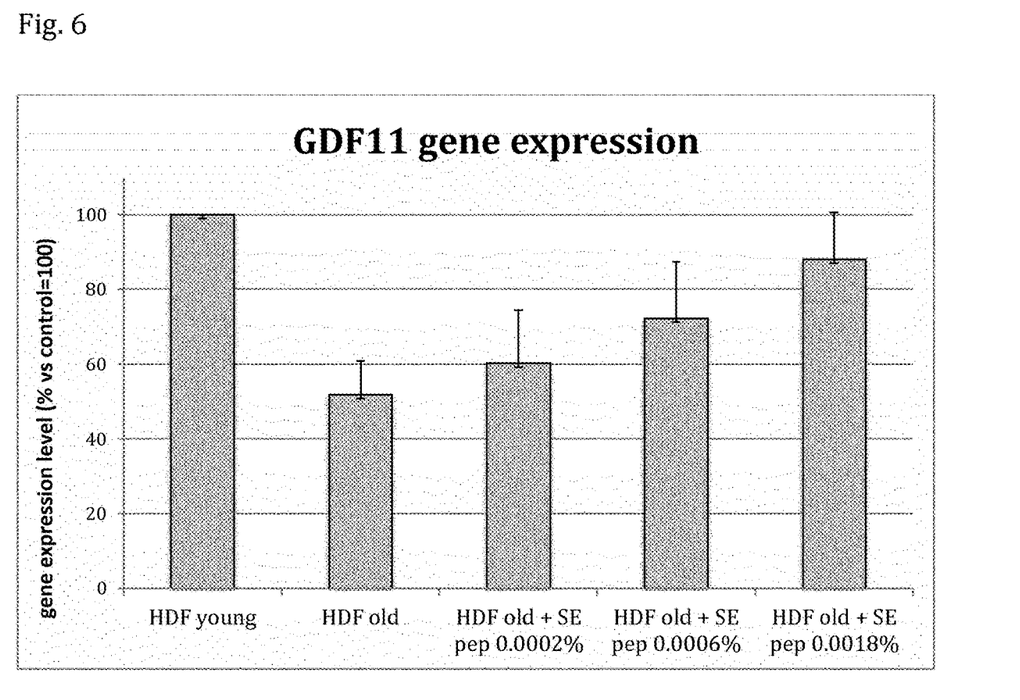
FIG. 6 shows the expression analysis of the gene GDF11 in young fibroblasts (HDF young) and old fibroblasts (HDF old), treated with different concentrations of *Lotus japonicus* somatic embryo peptides/sugars extract. The values shown in the graph are expressed as percentages compared to the control sample of non-treated young cells, established as 100%.

In order to assess whether the peptide/sugar extract derived from *Lotus japonicus* somatic embryos (the one with the best performance in the previous tests) was able to induce GDF11 gene even in aged fibroblasts, it was conducted a new experiment in which primary fibroblasts derived from 36 year-old patients (HDF old) were treated with various extract concentrations and the expression level of GDF11 was evaluated and then compared with the expression level of GDF11 in young fibroblasts (HDF young). As shown in FIG. 6, the peptide/sugar extract induced the expression of the GDF11 gene even in aged fibroblasts, in a dose-dependent manner, and almost restored the level of expression typical of the young fibroblasts. This result indicated that the extract of somatic embryos of *Lotus japonicus* was able to revert the phenotype of senescence of the cells through the activation of GDF11.

Effects of the Combination of the Three Extracts Derived from *Lotus japonicus* Somatic Embryos on the Expression of GDF11 Gene.

Figure 7:
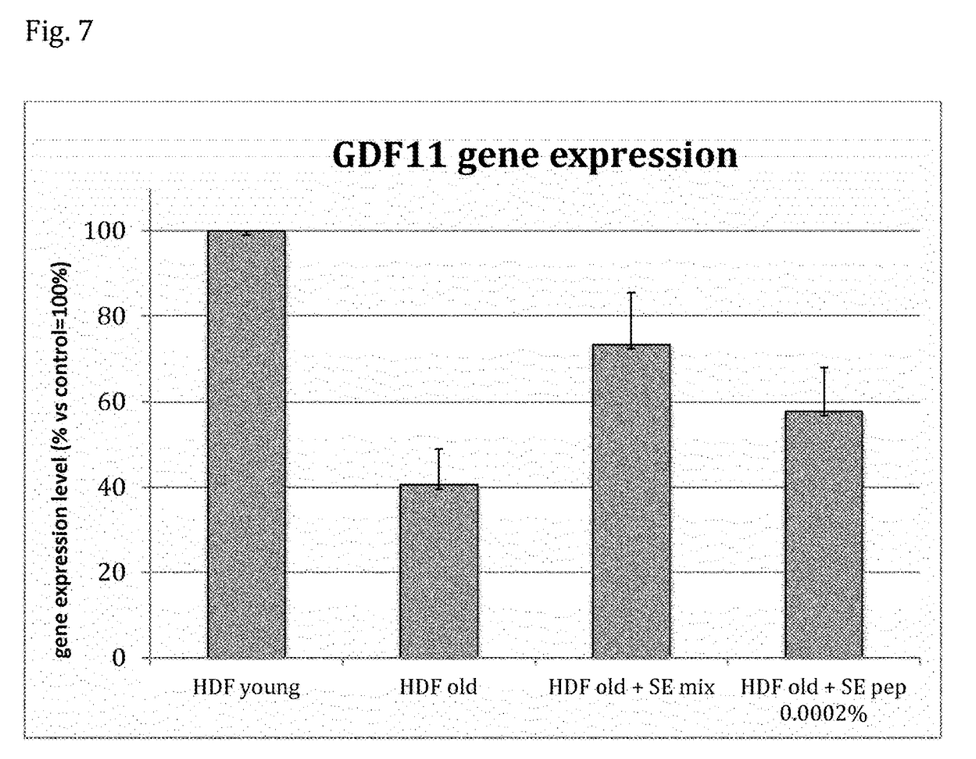
FIG. 7 shows the effect of the single extracts of *Lotus japonicus* somatic embryos and the mixture consisting of the union of the 3 extracts in ratio 1:1:1, on the expression of GDF11 gene in young (HDF young) and old (HDF old) fibroblasts. The values shown in the graph are expressed as percentages compared to the control sample of non-treated young cells, established as 100%.

In order to evaluate whether the effect of GDF11 was further increased by the treatment with all the extracts combined together, aged fibroblasts (HDF old) were treated with the mixture containing the 3 extracts in previously calculated effective concentrations (0.002% for water and ethanol extracts, and 0.0002% for the peptide/sugar extract) and with the peptide/sugar extract alone, for 6 hours. As shown in FIG. 7, the effect of the mixture containing the 3 extracts on the expression of GDF11 was significantly higher than that of the peptide/sugar extract alone, suggesting a synergic effect of the combination in this specific gene activation.

In conclusion, the mixture of the three extracts of *Lotus japonicus* somatic embryos was more effective in activating GDF11 than the peptide/sugar extract alone, thus inducing a stronger response in the anti-aging and rejuvenation processes in skin cells. Therefore, this mixture could be used as single active ingredient in cosmetic formulations dedicated to skin care.

CITED PAPERS (IN ALPHABETICAL ORDER)

1) Anderson O, Reissmann E, Ibanez C F (2006). Growth differentiation factor 11 signals through the transforming growth factor receptor ALK5 to regionalize the anterior-posterior axis. EMBO reports 7, 831-837.
2) Barbulova A, Apone F and Colucci G (2014). Plant cell cultures as source of cosmetic active ingredients. Cosmetics, 1, 94-104.
3) Fowler M. (1984). Plant cell culture: natural products and industrial application. Biotechnol. Genetic Engineer. Rev., 10 (2): 41-67.
4) Katsimpardiay L, Litterman N K, Schein P A, Miller C M, Loffredo F S, Wojtkiewicz G R, Chen J W, Lee R T, Wagers A J, Rubin L L. (2014) Vascular and neurogenic rejuvenating of the aging mouse brain by young systemic factors. Science, 344 (6184): 630-634.
5) Lavu S, Boss O, Elliott P J and Lambert P D (2008). Sirtuins—novel therapeutic targets to treat age-associated diseases. Nature Rev Drug Discover, 7: 841-853.
6) Lee E, Jin Y, Park J, Yoo Y, Hong S, Amir Z, Yan Z, Kwon E, Elfisk A, Tomlinson S, Halbritter F, Waibel T, Yun B and Loake G (2010). Cultured cambial meristematic cells as a source of plant natural products. Nature biotech, 28 (11): 1213-1217.
7) Loffredo F S, Steinhauser M L, Jay S M, Gannon J, Pancoast J R, Yalamanchi P, Sinha M, Dall'Osso C, Khong D, Shadrach J L, Miller C M, Singer B S, Stewart A, Psychogios N, Gerszten R E, Hartigan A J, Kim M J, Serwold T, Wagers A J and Lee RT1 (2013). Growth differentiation Factor 11 is a circulating factor that reverses age-related cardiac hypertrophy. Cell, 153 (4): 828-839.
8) Mao Z, Hine C, Tian X, Van Meter M, Au M, Vaidya A, Seluanov A, Gorbunova V (2011). SIRT6 promotes DNA repair under stress by activating PARP1. Science, 332 (6036): 1443-6.
9) Sinha M, Jang Y C, Oh J., Khong D., Wu E Y., Manohar R., Miller C., Regalado S G, Loffredo F S, Pancoast J R, Hirshman M F, Lebowitz J, Shadrach J L, Cerletti M, Kin M J, Serwold T, Goodyear L J, Rosner B, Lee R T, Wagers A J (2014). Restoring systemic GDF11 levels reverses age-related dysfunction in mouse skeletal muscle. Science, 344 (6184): 649-652.
10) Williams G, Zentar M P, Gajendra S, Sonego M, Doherty P, Lalli G. Transcriptional basis for the inhibition of neural stem cell proliferation and migration by the TGFβ-family member GDF11 (2013). Plos One, 8 (11): e78478.
11) Zschoernig B & Mahlknecht U (2008). SIRTUIN 1: regulating the regulator. Biochem Biophys Res Comm, 376: 251-255.

The invention claimed is:

1. A method of treating imperfections related to skin aging and inducing a skin tissue rejuvenation effect in a human subject, said method comprising topically applying at least one extract derived from somatic embryo-enriched plant cell cultures onto the skin of the subject, and wherein said somatic embryo-enriched plant cell cultures are plant cell cultures belonging to the species *Lotus japonicas, Citrus limon,* and *Rosa gardenia.*

2. The method Use according to claim 1, wherein said at least one extract is a hydrosoluble extract, obtained by a the process comprising:
   a) inducing plant cell suspension cultures to form somatic embryos:
   b) homogenizing the obtained somatic embryos in a salt water solution, obtaining a homogenate;
   c) separating the solid part from the liquid part of said homogenate, the liquid part constituting said hydrosoluble extract.

3. The method U-se according to claim 1, wherein said at least one extract is a liposoluble extract, obtained by the process comprising
   a) inducing plant cell suspension cultures to form somatic embryos;
   b) homogenizing the obtained somatic embryos in a salt water solution, obtaining a homogenate:
   c) separating the solid part from the liquid part of said homogenate, the liquid part constituting a hvdrosoluble extract; and
   d) extracting said solid part with a lipophilic solvent, obtaining said liposoluble extract.

4. The method according to claim 1, wherein said at least one extract is an extract rich in peptides and sugars, obtained by the process comprising:
   a) inducing plant cell suspension cultures to form somatic embryos;
   b) homogenizing the obtained somatic embryos in a salt water solution, obtaining a homogenate;
   c) separating the solid part from the liquid part of said homogenate the liquid part constituting a hydrosoluble extract; and
   d) treating said solid part with proteolytic enzymes in acid solution in order to hydrolyze the glycoproteins of the cell walls of the somatic embryos, obtaining said extract rich in peptides and sugars.

5. The method according to claim 1, wherein said at least one extract comprises a composition comprising a hydrosoluble extract, a liposoluble extract and an extract rich in peptides and sugars.

* * * * *